United States Patent [19]

McCroskey et al.

[11] Patent Number: 5,271,895
[45] Date of Patent: Dec. 21, 1993

[54] TEST STRIP

[75] Inventors: Ralph P. McCroskey, Carmel, Ind.; Helmut E. C. Freitag, Weinheim, Fed. Rep. of Germany; Mary C. Smith, Indianapolis; Kenneth J. Dean, Carmel; Stephanie Secrest, Bloomington; Lee Bouse, Inpls, all of Ind.

[73] Assignee: Boehringer Mannheim Corporation, Indianapolis, Ind.

[21] Appl. No.: 33,451

[22] Filed: Mar. 18, 1993

Related U.S. Application Data

[63] Continuation of Ser. No. 661,788, Feb. 27, 1991, abandoned.

[51] Int. Cl.$^5$ .................... C07N 21/00; C12M 1/34
[52] U.S. Cl. .......................... 422/58; 422/61; 422/57; 422/56; 422/101; 435/970; 435/291
[58] Field of Search ............... 422/56, 57, 58, 60, 422/61, 101; 436/169, 170; 435/7.92, 7.94, 291, 970, 975

[56] References Cited

U.S. PATENT DOCUMENTS

| | | | |
|---|---|---|---|
| 4,857,273 | 8/1989 | Stewart | 422/68.1 |
| 4,876,067 | 10/1989 | Deneke et al. | 422/56 |
| 4,956,302 | 9/1990 | Gordon et al. | 436/161 |
| 4,981,786 | 1/1991 | Dafforn et al. | 435/7 |
| 5,037,736 | 8/1991 | Freitag et al. | 435/7.9 |
| 5,053,197 | 10/1991 | Bowen | 422/58 |
| 5,059,394 | 10/1991 | Phillips et al. | 422/68.1 |
| 5,114,673 | 5/1992 | Berger et al. | 422/56 |

FOREIGN PATENT DOCUMENTS 0271854 6/1988 European Pat. Off. .......... 435/970

*Primary Examiner*—Robert J. Warden
*Assistant Examiner*—T. A. Trembley
*Attorney, Agent, or Firm*—Max J. Kenemore; D. Michael Young; Marilyn L. Amick

[57] ABSTRACT

The operative site of an assay device is dosed with a controlled volume of a liquid specimen by a holding device which holds the controlled volume of specimen in contact with the operative site, although the holding device remains out of contact with the operative site. A sink device is in contact with the margin of the holding device and moves excess specimen away from the holding device. In one embodiment the device makes possible a non-wipe teststrip architecture. The device can be used in the detection of analytes including glucose or cholesterol in blood or urine and can be interrogated visually, optically or electrically, depending on the reagent used at the operative site.

14 Claims, 3 Drawing Sheets

TEST STRIP

This is a continuation of copending Ser. No. 07/661,788, filed on Feb. 27, 1991, now abandoned.

BACKGROUND OF THE INVENTION

1. Field of the Invention

This invention relates generally to assays for determining the presence or concentration of an analyte in a fluid sample and, more specifically, to improvements in the architecture of test strip devices used in such assays. The invention relates especially to such devices for use in the determination of analytes in blood.

2. Description of the Prior Art

Teststrips are not new. Their use in determining the presence or concentration of an analyte, such as glucose, in a sample, such as blood or urine, is well accepted. Generally, teststrips operate on the principle that the analyte causes a detectable change which can be used to determine the presence or concentration of the analyte.

Some such teststrips indicate the presence or amount of an analyte by a degree of color change in a reagent. Some color change teststrips are intended to be read visually while others are intended to be interrogated by an electronic meter, such as a reflectance photometer which looks for shifts in color intensity or reflectance at a specific wavelength.

In other teststrips the presence or amount of an analyte is indicated by a change in the electrical condition of a reagent. Such teststrips are commonly known as biosensors.

Such meters are well known and normally contain a means for converting the reflectance reading to an analyte concentration value. Such a means may be, for example, a comparator means for comparing the signal generated by the reflectance photometer with a table to determine the analyte concentration related to a specific signal. It may also be software which makes use of an algorithm to convert such a signal to such a value. Such meters also normally include a display device for displaying the value.

When used to assay for an analyte in blood, many well known teststrips require that the indicator portion of the strip be dosed with blood and then washed, blotted or wiped free of excess blood after a specific reaction time. The blotting or wiping requirement is sometimes required to expose the reagent site for either visual or meter interrogation. Wiping is also normally required to avoid fouling a meter with excess blood whenever a teststrip is to be inserted into a meter for optical interrogation.

Although great commercial success has been achieved based on teststrips which must be wiped or blotted, there is room for improvement to achieve both more accurate assays and greater customer acceptance. The blotting or wiping step is believed to be a source of error in teststrip assays because some users wipe too lightly, leaving a layer of blood covering the reaction site. This layer of blood can mask or confuse the color change in the analyte, resulting in incorrect readings. Likewise, other users wipe the teststrip with too great a pressure, removing not only excess blood but also some of the reagent material, also resulting in an incorrect determination. The timing of the wiping step is also sometimes important. Incorrect readings can result if the wiping is accomplished too soon or too late.

The wiping step is also seen as an inconvenience by teststrip users who are required to provide the wiping material, such as cotton, and also to dispose of used wiping materials.

Much effort has been invested in forming a teststrip which does not have to be wiped and which will hold a useful amount of specimen at an operative site. One prior art design involves a teststrip having located, near its reagent site, a wick which directs excess specimen into a sink, thus avoiding the need to wipe away the excess. However, most such wicks draw away too much specimen, leaving too little at the reaction site. Many other efforts have been made to hold an operative amount of specimen at the reaction site while at the same time removing excess specimen without wiping. One example of such prior art designs uses soluble barrier layers to temporarily separate the reaction site from the wick; however, such designs present large manufacturing and materials selection problems.

A commercially available meter / teststrip system which attempts to solve the wiping problem requires that the teststrip be positioned in the meter and carefully aligned before a drop of blood is touched to a blood-receiving site on the strip. Some of the disadvantages of the wiping step have been avoided by this system; however, dosing of the teststrip in the meter by diabetics, who are sometimes unsteady and possessed of poor eyesight, is seen as a new disadvantage. Such persons also sometimes have trouble accurately placing a blood drop from a finger prick onto the small target area of the teststrip without getting blood on the surrounding meter parts. This excess blood can foul the mechanical and optical workings of the meter or lead to contamination in a clinical setting.

There exists a need for a teststrip which both hold a controlled amount of specimen at an operative site and avoids the requirement for wiping away excess sample and which also minimizes the possibility of fouling the meter with excess or badly applied sample.

SUMMARY OF THE INVENTION

It is an object of the present invention to eliminate the need for wiping away of excess blood.

It is another object of the present invention to facilitate the dosing of test strips to be read by reflectance meters.

It is another object of the present invention to insert a dosed teststrip into a meter without fouling the meter with excess sample fluid to the extent that the operation of the meter is compromised.

These and other objects are accomplished by an assay device which includes a holding means for holding a controlled volume of specimen at an operative site during the performance of the assay and a sink means for removing excess specimen from the holding means.

The present invention is based on the discovery that the combination described above will maintain a reactive amount of sample in contact with the reagent while removing excess sample and avoid the need for wiping the teststrip.

This inventive combination of a holding means and a sink means is useful in a variety of assays. For example, this combination may be used to avoid the need to wipe a teststrip while holding a controlled volume of blood against a fleece or filter means in the teststrip which separates red blood cells from serum. In such an assay the serum is normally transported by the fleece or filter means to a reagent which indicates the presence or concentration of an analyte in the serum; although, in some assays, the reagent is located in the fleece or in the filter means.

In other assays, the combination holds a controlled amount of specimen directly against a reagent layer which changes color to indicate the presence or concentration of an analyte. Excess specimen is drawn into the sink means so that the need to wipe is eliminated.

The holding means may be any suitable material which will hold a controlled volume of specimen against an operative site. The controlled volume is determined by the size of the holding means, the size of the operative site and the space therebetween. The volume will, in the case of each assay, also be effected by the surface tension of the specimen and the hydrophilic or hydrophobic nature of the holding means and of the operative site.

An assay which incorporates this invention may have many embodiments. The operative site to be dosed may be, for example, a filter or membrane which includes a reagent system which makes a detectable change in response to the presence of an analyte. The operative site may be a layer of material which changes its electrical characteristics in response to the presence of an analyte, such as in a biosensor. The operative site can also be a layer of reagent materials which is held on a support.

A preferred embodiment which is made possible by the present discovery is a novel teststrip architecture. As described below, it is used in determining the presence and concentration of glucose in whole blood. It will be clear to one of ordinary skill in the test strip art that this embodiment could be adapted for use with other reagents and that the invention is capable of a variety of embodiments in which an operative site is dosed.

In the preferred embodiment a controlled volume of whole blood is held directly against a reagent layer which has been coated on a transparent support layer. The glucose in the whole blood reacts with the reagent, changing the reflectance characteristics of the reagent layer. This change in reflectance is noted by a reflectance photometer which interrogates the reagent layer through the transparent support.

The holding means may be made from any useful material. In the preferred embodiment, the holding means is formed from a netting which is woven from a polyester monofilament and treated with a surfactant. The netting is preferred because it has sufficient stiffness to resist being drawn down onto the reagent layer by surface tension forces in the specimen. Contacting of the operative site by the netting frustrates the dosing feature of the invention by reducing the controlled volume. Such touching could also trap bubbles on the reagent surface, resulting in uneven dosing of the reagent layer. The stiffness of the preferred material also provides some protection from accidental disturbance of the reagent layer by a user.

The surfactant treatment of the netting aids in the even spreading of the specimen over the reagent layer by modifying the surface tension characteristics of the holding means.

The proper distance of the holding means from the operative site will vary depending on such factors as the amount of specimen needed and the dimensions of the site. For example, in a teststrip of the inventive design, described above, having a reagent layer of about $10 \times 6$ mm in length and width, it is desirable to hold about 13 microliters of whole blood against the site during the assay. A spacing suitable to control the volume of blood to about 13 microliters is achieved by an average distance between the reagent layer and the holding means of about 100 microns. It is understood that the distance between the operative site and the dosing side of the holding means may vary due to manufacturing imprecision, etc. Such variance is not detrimental to the invention as long as the dosing of the specimen is relatively uniform across the reagent layer. Other spacings can be calculated for other sizes of reagent layers and other stoichiometric requirements by simple mathematics.

However, regardless of the desired volume of specimen, the holding means should be maintained sufficiently close to the operative site to result in an even distribution of specimen over the site. Excessive distance of the holding means from the operative site will result in the specimen being drawn to the edges and to spots within the operative site, leaving some areas undosed. This creates uneven dosing.

The sink means is for transporting excess sample away from the receiving surface of the holding means. Excess sample is sample in excess of that held in the space between the holding means and the operative site. Removal of the excess sample from the sample receiving surface provides the "no-wipe" feature of a teststrip which incorporates the present invention. Removal of excess sample into the sink means avoids fouling of the components of a meter into which the teststrip is inserted for interrogation.

Normally, this sink means will include a wicking portion which preferably contacts the holding means on its sample receiving side at its margin. The sink means may be out of actual contact with the holding means as long as it is positioned so as to remove excess specimen from the holding means.

The sink means also normally includes a waste portion for holding the excess specimen. The waste portion is in contact with the wick portion but is normally not in contact with the holding means.

The sink means can be made from any suitable material. For example, good results have been obtained using a cellulose material, such as filter paper. However, a preferred material is a woven or non-woven polyester fabric which has been treated with a surfactant. The fabric is also preferred because it is less readily squeezable and would be less likely to release excess specimen into a meter if accidentally squeezed by a customer.

A common analyte for determination by teststrips employing the present invention is glucose in human or animal blood. However, the analyte could just as readily be for any one of a number of other analytes in a number of other types of samples such as, for example, cholesterol in blood or glucose in urine, and glucose or alcohol in food or in manufacturing liquids.

The novel teststrip architecture mentioned above will typically have a reagent layer containing chemistry which produces a change in reflectance upon reacting with an analyte in a sample. The particular type of reagent is not critical to the operation of the present invention. Several different such reagent layers are known.

One such reagent which is particularly useful in connection with the present invention is described in U.S. Pat. No. 4,929,545, issued May 29, 1990 to Freitag. This reagent is of special interest because red blood cells in contact with one side of a reagent layer made from this material normally will not interfere with optical interrogation of the layer from the opposite side. Removal or filtration of cellular material from the plasma in blood is not necessary when this reagent is used. Other reagents which are well known in the art will readily come to the mind of the skilled practitioner.

In a preferred embodiment of the present invention the reagent of Freitag is coated on a support layer through which color change in the reagent can be observed from the side of the reagent layer which is opposite the side on which whole blood is applied. Although a visible color change can be observed in this manner, the degree of change in reflectance for this specific reagent is best determined when interrogated by reflected light of a specific wavelength through a support layer which is transparent at that wavelength.

Any suitable surfactant can be used in the preferred embodiment to treat the holding means so that it aids in spreading the specimen on the reagent layer. The specific surfactant may depend on the nature of the sample. Suitable surfactants include commercially available detergents such as Triton X-100, Aerosol TO, Tween 20 and Igepal CO-997.

This inventive architecture may be adapted for use in a teststrip which can be interrogated by a reflectance photometer. Normally this is accomplished by sandwiching the reagent layer, supported on a transparent support, the holding means and the sink means between solid carrier layers. The solid layers have ports which are substantially opposite each other and substantially overlay the reagent layer and the holding means. In such a structure the side on which the port gives access to the holding means is referred to as the application side, and the side on which the port gives access to the support for the reagent layer is referred to as the interrogation side.

In operation, a specimen such as a drop of blood from, for example, a pricked finger is applied to the sample receiving side of the holding means. The holding means passes the blood into the space between its applicator side and the reagent layer where the blood spreads to fill the space. Any excess fluid which remains above the surface of the holding means comes into contact with the wicking portion of the sink means and is drawn by capillary action away from the sample receiving area. Excess sample which wells above the application port will also be drawn out of the port and into the sink means.

The holding means contacts the specimen before the specimen contacts the wicking portion of the sink means so that an amount of specimen is drawn through the holding means to fill the space of predetermined volume between the applicator surface of the holding means and the reagent layer before the sink means draws the excess sample into the its waste portion.

In a preferred embodiment, the device is then inserted into a meter which interrogates the reagent layer through its transparent support to determine any shift in reflectance in the reagent layer due to the presence or concentration of an analyte, such a glucose.

In an assay device according to the present invention it is not necessary to wipe blood or other sample fluid away from the application port in order to observe the reaction layer because the reflectance reading is taken on the side opposite the blood or specimen application site. However, in the absence of the sink means, excess blood which stands above the surface of the solid support on the application side or which is squeezed out of the application port or out of the sides of the meter by tilting or jarring of the strip or meter or by any clamping operation inside the meter would eventually foul the mechanical interior of the meter. This potential problem is avoided by the sink means which moves any such excess specimen or blood away from the sample receiving area and holds it there so that the likelihood of excess sample fouling the mechanical interior of a meter is substantially eliminated.

In a preferred embodiment a fluid impermeable channel means directs the excess liquid sample to the wicking portion of the sink means and away from the waste portion of the sink means which may be near or adjacent the operative site. The purpose of this is to avoid accumulation of excess sample fluid in the sink means near the operative site where it could be squeezed out the sides of the strip and into the meter mechanism by tilting, jarring or by clamping operations of the meter mechanism.

Reflectance meters which are suitable for interrogating the present device and correlating any color change in the reagent layer with the presence or concentration of an analyte of interest are known.

The present invention will now be described with reference to the accompanying drawings which are intended to be exemplary and illuminating but not limiting. Other specific embodiments which are within the scope of the accompanying claims will be evoked by the specific embodiments of these drawings.

DETAILED DESCRIPTION

Figure 1:
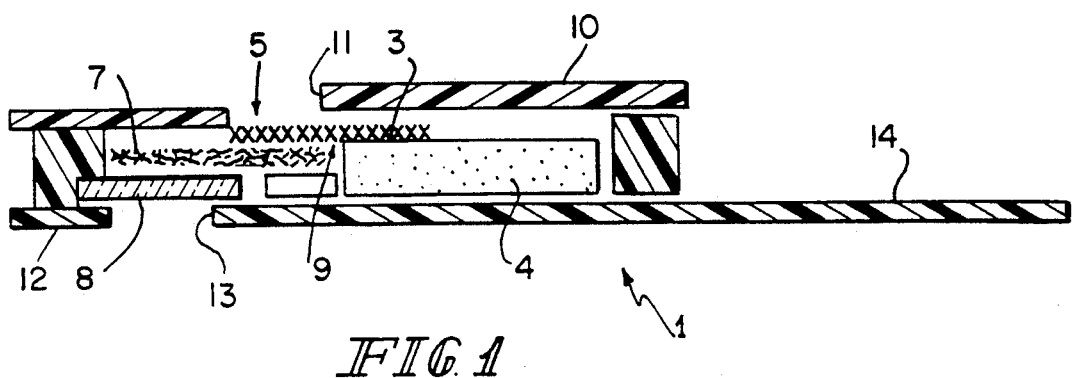
FIG. 1 shows in cross-sectional side view of one teststrip architecture which includes the present invention and wherein the operative site is a filter.

Referring more specifically to FIG. 1 there is shown a schematic, cross-sectional, exploded side view of teststrip 1 which includes a holding means and a sink means in accordance with the present invention. Holding means 2 in this embodiment is a net which is contacted at its periphery 3 by cellulosic sink material 4.

Holding means 2 is spaced apart from operative site 5 to create a space of controlled volume 6 therebetween. In this embodiment operative site 5 is a location on the surface of fleece layer 7. Fleece layer 7 extends between operative site 6 and reagent holder 8. Reagent holder 8, in this embodiment, is a cellulosic filter paper which has been impregnated with reagents which act together to produce a color change in the presence of an analyte, such as glucose, in a specimen, such as blood plasma.

The embodiment of teststrip 1 is especially suited for use with reagent combinations wherein the color change would be difficult to interrogate in the presence of colored particulates, such as red blood cells. When this embodiment is used in glucose determination, whole blood is applied to the top of holding means 2 which passes the whole blood into the controlled space between its dosing side 9 and operative site 5. Whole blood in excess of the amount held in controlled volume 6 by surface tension moves along holding means 2 to periphery 3 where it is absorbed by sink 4, which does not contact operative site 5. Fleece 7, which can be a glass fleece as described in U.S. Pat. Nos. 4,816,224 and 4,477,575 to Vogel, separates the red blood cells at operative site 5 from whole blood and transports the remaining blood plasma to reagent holder 8 where glucose, for example, in the plasma causes a color change which can be interrogated either with the naked eye or by means of a reflectance photometer, which will see the color change as a change in reflectance.

Teststrip 1 includes first cover 10 on its sample application side. First port 11 in first cover 10 is positioned substantially opposite operative site 5 so that the specimen can be applied to holding means 2 at a site which is closer to operative site 5 than to periphery 3 where sample will be drawn into sink 4.

Teststrip 1 also includes second cover 12 on its interrogation side where second port 13 exposes reagent holder 8 to visual or optical interrogation. Second cover 12 includes handle portion 14 for use in manipulating teststrip 1 during sample application and interrogation.

Figure 2:
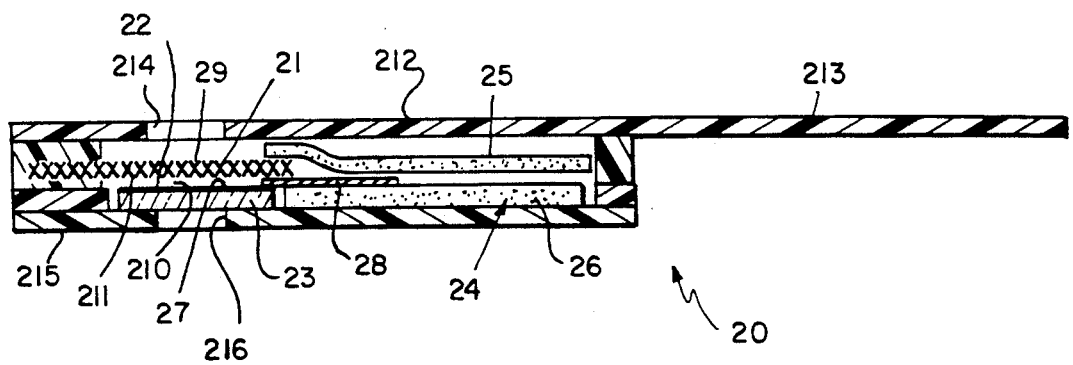
FIG. 2 shows in cross-sectional side view another teststrip architecture which includes the present invention and wherein the operative site is a reagent layer supported on a transparent carrier and wherein the sink means includes a cellulosic material.

FIG. 2 shows a schematic, cross-sectional, exploded side view of teststrip 20 which shows another teststrip architecture which includes the present invention.

Holding means 21 is a woven net material which is spaced apart from reagent layer 22 on transparent support 23. Sink means, generally designated 24, includes a non-woven fabric wicking portion 25 and cellulosic waste portion 26.

Wicking portion 25 contacts the periphery of holding means 21, and waste portion 26 is held out of contact with operative site 27. Barrier 28 separates waste portion 26 from the general area of operative site 27. Sample, such as a drop of whole blood applied to application side 29 of holding means 21 will be passed through it and held by surface tension forces in controlled volume 210 between dosing side 211 of holding means 21 and reagent layer 22.

Sample in excess of controlled volume 210 will be drawn away from the periphery of holding means 21 by wicking portion 25 of sink 24 and stored in waste portion 26. Barrier 28 works with transparent support 23 to isolate waste portion 26 from the operative site.

Reagent layer 22 includes reagents in which a color change on the side adjacent the transparent support will not be masked by contacting of the layer on the side opposite the transparent support with red blood cells. The reagent of Freitag, mentioned above, is suitable for use in such an embodiment. An analyte, such as glucose causes a color change in reagent layer 22 which is visible through transparent support 23. Reagent layer 22 can be interrogated for color change through support 23 either visually or optically.

First support 212 covers the application side of holding means 21 and includes handle portion 213. First support 212 has first port 214 substantially overlying holding means 21 and substantially opposite reagent layer 22.

Second support 215 covers transparent support side of teststrip 20. Second support 215 has second port 216 which exposes the transparent support for visual or optical interrogation.

In operation, a specimen, such as whole blood from a pricked finger is applied to application side 29 of holding means 21. The specimen is passed through holding means 21 and spread by surface tension forces to fill controlled volume 210 so that a controlled amount of specimen is held against reagent layer 22.

Specimen in excess of controlled volume 210 is drawn from the periphery of holding means 21 and moved by capillary forces into sink portion 26 of sink means 24.

If the specimen is whole blood and the assay is for glucose, the whole blood is held against reagent layer 22 so that glucose in the blood will react with the reagents in reagent layer 22 to cause a color change which can be observed visually or optically through transparent support 23.

Figure 3:
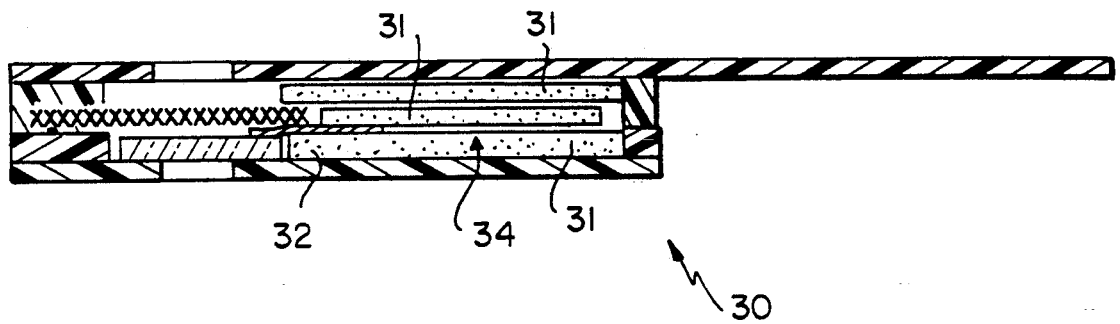
FIG. 3 shows a cross-sectional elevation of a teststrip architecture which includes the present invention and in which the sink means is formed from fabric layers.

Barrier 28 directs excess blood toward the portion of sink means 24 which contacts the margin of holding means 21 to prevent an accumulation of excess blood in the portion of sink means 24 which is closest to holding means 21. This reduces the possibility that, if teststrip 20 is jarred, tilted or squeezed, such as by a clamp in a meter, excess blood would exit teststrip 20 and foul the meter mechanism. FIG. 3 shows a teststrip generally designated as 30 which which incorporates an architecture based on the present invention. Teststrip 30 is similar to teststrip 20 of FIG. 2 except that the sink means, generally designated 34, is formed from layers 31 of fabric. As mentioned above, the fabric may be woven or not woven, and is preferably treated with a surfactant to make it compatible with the specimen. The fabric of FIG. 3 is preferred over the cellulosic material of FIG. 2 because it is less compressible and, thus, less likely to release excess specimen from waste portion 32 when clamped in a meter.

Figure 4:
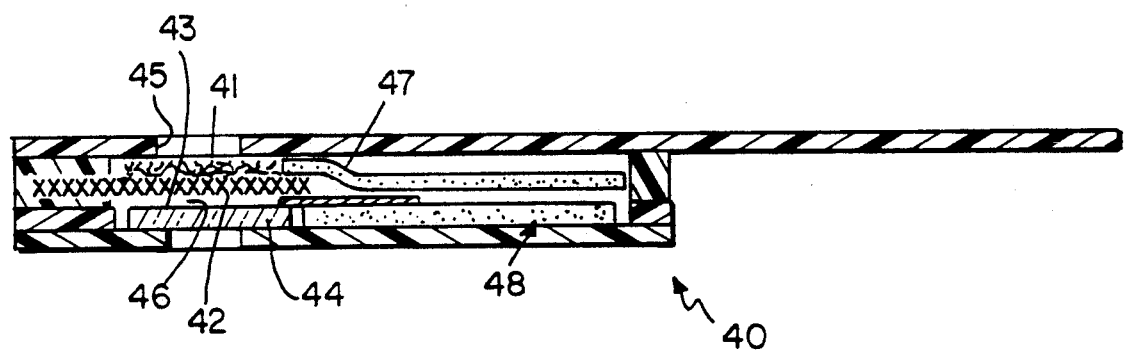
FIG. 4 shows a cross sectional elevation of a teststrip which includes the present invention and in which the specimen is filtered before contacting the holding means.

FIG. 4 also shows a teststrip, generally designated as 40, which has an architecture based on the present invention. FIG. 4 is similar to FIG. 2 except that filter medium 41 covers holding means 42. Such a structure is useful when reagent layer 43 is made from a material in which the color change caused by the analyte would be masked by the presence of colored material, such as red blood cells, in contact with the side of reagent layer 43 opposite transparent support 44.

When the specimen is whole blood, it is applied to filter 41 through port 45. Red blood cells are held back by filter 41 and plasma passes through filter 41 and holding means 42 to fill controlled volume 46 so that a controlled amount of the plasma is held against reagent layer 43.

Whole blood in excess of the amount needed to supply plasma for controlled volume 46 is drawn away from the application site by wicking portion 47 of sink means 48.

Figure 5A:
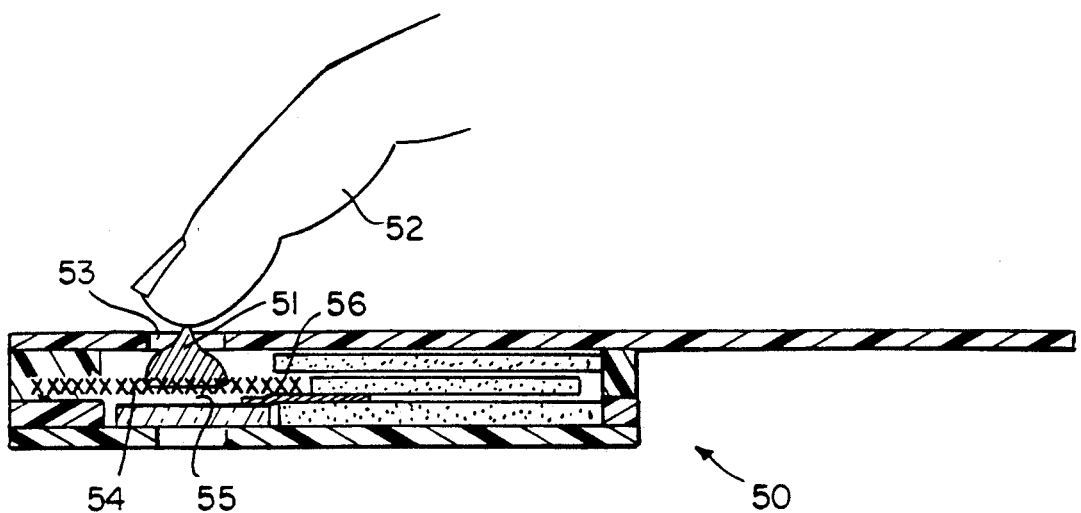
FIGS. 5a, 5b and 5c show in cross sectional elevation the operation of the teststrip of FIG. 3 during an assay for a component of blood.

FIG. 5a shows a drop of blood 51 from pricked finger 52 being applied to teststrip 50, which is similar to teststrip 30 of FIG. 3, through first port 53. Drop 51 passes through holding means 54 toward space 55 of controlled volume. Drop 51 also begins to move laterally toward margin 56 of holding means 54.

Figure 5B:
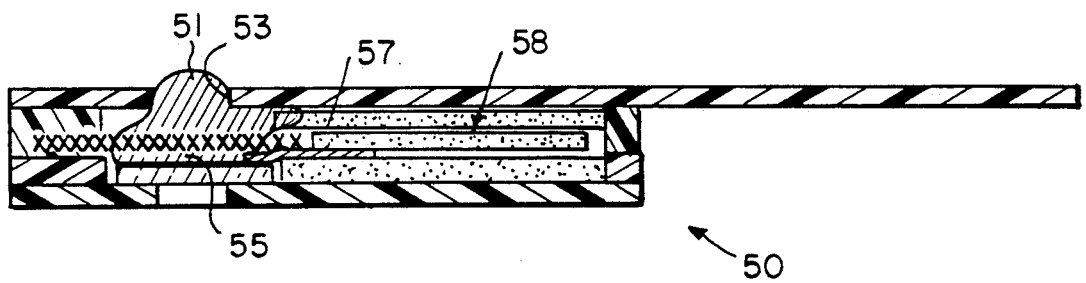

FIG. 5b shows drop 51 having been drawn into teststrip 50 so that space 55 is filled with a controlled volume of whole blood and whole blood has also begun to contact wicking portion 57 of sink means 58. A portion of drop 51 remains above the edge of first port 53.

Figure 5C:
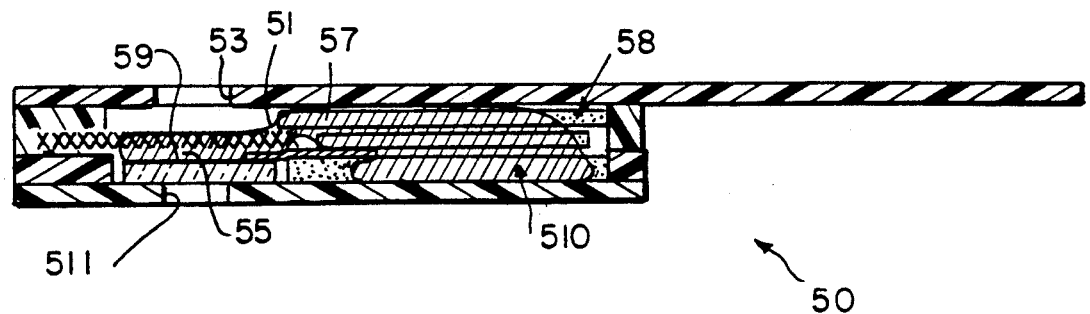

FIG. 5c shows a controlled volume of drop 51 filling space 55 in contact with reagent layer 59. Blood in drop 51 in excess of the amount needed to fill space 55 is absorbed by wicking portion 57 and passed along to waste portion 510 of sink means 58.

If teststrip 50 is used in an assay for glucose, reagent layer 59 will change in color depending on the presence and concentration of glucose. This color change can be observed, for example, as a change in reflectance by a reflectance photometer which interrogates reagent layer 59 through second port 511.

It will be apparent to one of ordinary skill in the test strip technology that the reagent layer of FIGS. 2-5 could just as readily be a biosensor reagent which is interrogated by electrical means, and such an embodiment is intended to be within the scope of the appended claims.

The present invention has been disclosed in the above teachings and drawing with sufficient clarity and conciseness to enable one skilled in the art to make and use the invention, the know the best mode for carrying out the invention and to distinguish it from other inventions and from what is old. Many variations and obvious adaptations of the invention will readily come to mind, and these are intended to be contained within the scope of the invention as claimed below.

What is claimed is:

1. A teststrip for use in an assay to determine the presence or concentration of analyte in a liquid specimen, the teststrip comprising:
   (a) a reagent layer;
   (b) a surfactant treated netting, overlaying the reagent layer, having openings of a size sufficient to pass a liquid specimen;
   (c) means for maintaining the surfactant treated netting in a spaced-apart relationship with the reagent layer so as to define a space of controlled volume therebetween such that when liquid specimen is applied to the surfactant treated netting a controlled volume thereof will pass through the surfactant treated netting and be held by surface tension in substantially uniform contact with the reagent layer; and
   (d) a sink means, positioned at the periphery of the surfactant treated netting, which is capable of absorbing and holding liquid specimen which is not held in the space of controlled volume.

2. A teststrip according to claim 1 wherein the reagent layer makes a detectable change in response to contact with an analyte in the specimen.

3. A teststrip according to claim 2 wherein the detectable change is in the electrical characteristics of the reagent layer.

4. A teststrip according to claim 2 wherein the detectable change is in the reflectance characteristics of the reagent layer.

5. A teststrip according to claim 1 wherein the surfactant treated netting is made of a woven polyester.

6. A teststrip according to claim 1 wherein the sink means is made from material selected from the group consisting of cellulosic materials, woven and nonwoven fabrics and combinations thereof.

7. A teststrip according to claim 6 wherein the material is treated with a surfactant.

8. A teststrip according to claim 1 wherein the surfactant treated netting is at least partially covered by a filter means for separating components of the specimen prior to contact with the surfactant treated netting.

9. A teststrip according to claim 8 wherein the filter means is a glass fleece.

10. A teststrip wherein the construction of claim 1 is contained between first and second supports.

11. A teststrip according to claim 10 wherein at least one of the first and scorn supports includes a handle portion for manipulating the teststrip.

12. A teststrip wherein the construction of claim 1 is held between first and second supports, at least one of which supports is elongated to function as a handle for manipulating the teststrip, wherein the first and second supports include openings which are substantially opposite one another and which overlay at least the surfactant treated netting and the reagent layer, the opening overlying the surfactant treated netting functioning as a specimen application port and the opening overlying the reagent layer functioning as an interrogation port.

13. The teststrip of claim 1 wherein the reagent layer is supported on a transparent support.

14. The teststrip of claim 1 which additionally includes a barrier means positioned in contact with the reagent layer and the sink means so as to resist transfer of liquid sample from the sink means to the reagent layer.

* * * * *